(12) United States Patent
Baillot et al.

(10) Patent No.: US 7,383,129 B1
(45) Date of Patent: Jun. 3, 2008

(54) METHOD AND SYSTEM FOR GEO-REFERENCING AND VISUALIZATION OF DETECTED CONTAMINANTS

(75) Inventors: Yohan Baillot, Reston, VA (US); Patrick Louis Ponsardin, Placitas, NM (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 34 days.

(21) Appl. No.: 11/516,545

(22) Filed: Sep. 7, 2006

(51) Int. Cl.
*G01N 21/17* (2006.01)

(52) U.S. Cl. .................. 702/2; 702/5; 702/19; 702/22; 702/28

(58) Field of Classification Search ............ 702/2, 702/5, 19, 22, 28
See application file for complete search history.

(56) References Cited

U.S. PATENT DOCUMENTS

| | | | | |
|---|---|---|---|---|
| 5,319,547 A | * | 6/1994 | Krug et al. .................. 705/13 |
| 6,026,135 A | * | 2/2000 | McFee et al. ................ 376/159 |
| 6,166,744 A | | 12/2000 | Jaszlics et al. |
| 6,281,970 B1 | * | 8/2001 | Williams et al. .......... 356/141.4 |
| 6,608,559 B1 | | 8/2003 | Lemelson et al. |
| 6,788,407 B1 | * | 9/2004 | Higdon et al. ............. 356/301 |
| 6,853,328 B1 | | 2/2005 | Guice et al. |
| 6,903,752 B2 | | 6/2005 | Ebersole et al. |
| 6,941,806 B2 | | 9/2005 | Burns et al. |
| 6,946,671 B2 | | 9/2005 | Smith et al. |
| 6,947,064 B1 | * | 9/2005 | Hahn et al. ................ 701/301 |
| 7,058,509 B2 | | 6/2006 | Sohl, III et al. |
| 7,084,746 B2 | * | 8/2006 | Miyazaki et al. ........... 340/436 |
| 2007/0273610 A1 | | 11/2007 | Baillot |

* cited by examiner

*Primary Examiner*—Donald E McElheny, Jr.
(74) *Attorney, Agent, or Firm*—Edell, Shapiro & Finnan, LLC

(57) ABSTRACT

A system and method are provided for visualizing a scene that is monitored for substance contamination. The scene is scanned with a substance detector to detect a substance, such as a harmful chemical or biological substance. The position of the substance is determined. Graphical element data that represents the detected substance in the scene is generated. A displayed view of the scene is augmented with the graphical element data based on the position of the detected substance to show the detected substance in the view of the scene and provide the user with the location and type of detected substance shown with reference to the environment.

37 Claims, 5 Drawing Sheets

METHOD AND SYSTEM FOR GEO-REFERENCING AND VISUALIZATION OF DETECTED CONTAMINANTS

FIELD OF THE INVENTION

The present invention relates to displaying information pertaining to detected substances, such as at a contaminated scene.

BACKGROUND OF THE INVENTION

In the field of chemical or biological sensing or detecting, it is desirable to quickly detect substances at a contaminated scene and report information about the substances in order to prevent others from coming into contact or influence with the detected substance. There are standoff chemical detectors heretofore known that display information associated with the detection process independently from the scene where the chemicals are detected.

There are many shortcomings associated with the above-mentioned devices. Unless the contaminated scene is properly marked, a user carrying and controlling the detection equipment is the only one that can confirm the presence or absence of a substance at a specific location by performing a real-time measurement at the given location. The user carrying and controlling the detection equipment relies only on memory and visual markers to conduct a high spatial resolution delineation of the contamination patch. To visualize and remember the exact location of threat-chemical detection events, the user needs to physically mark the location of these events with a chemical-specific marking. Thus, the chance that the contaminated scene can become disrupted is high. Further, for large search/detection missions that can include walls, floors, and ceilings, the task of keeping track of already surveyed areas becomes quickly intractable.

No substance detection system is heretofore known that provides for real-time AR display of a scene as it is being scanned for contaminations.

SUMMARY OF THE INVENTION

Briefly, a system and method are provided for visualizing a scene that is monitored for substance contamination. The scene is scanned with a substance detector to detect a substance, such as a harmful chemical or biological substance. The positions of each detected sample of the substance are determined. Graphical element data that represents the detected substance in the scene is generated. A displayed view (or map image data) of the scene is augmented with the graphical element data based on the position of the detected substance to show the detected substance in the view (or map image data) of the scene.

DETAILED DESCRIPTION

Figure 1:
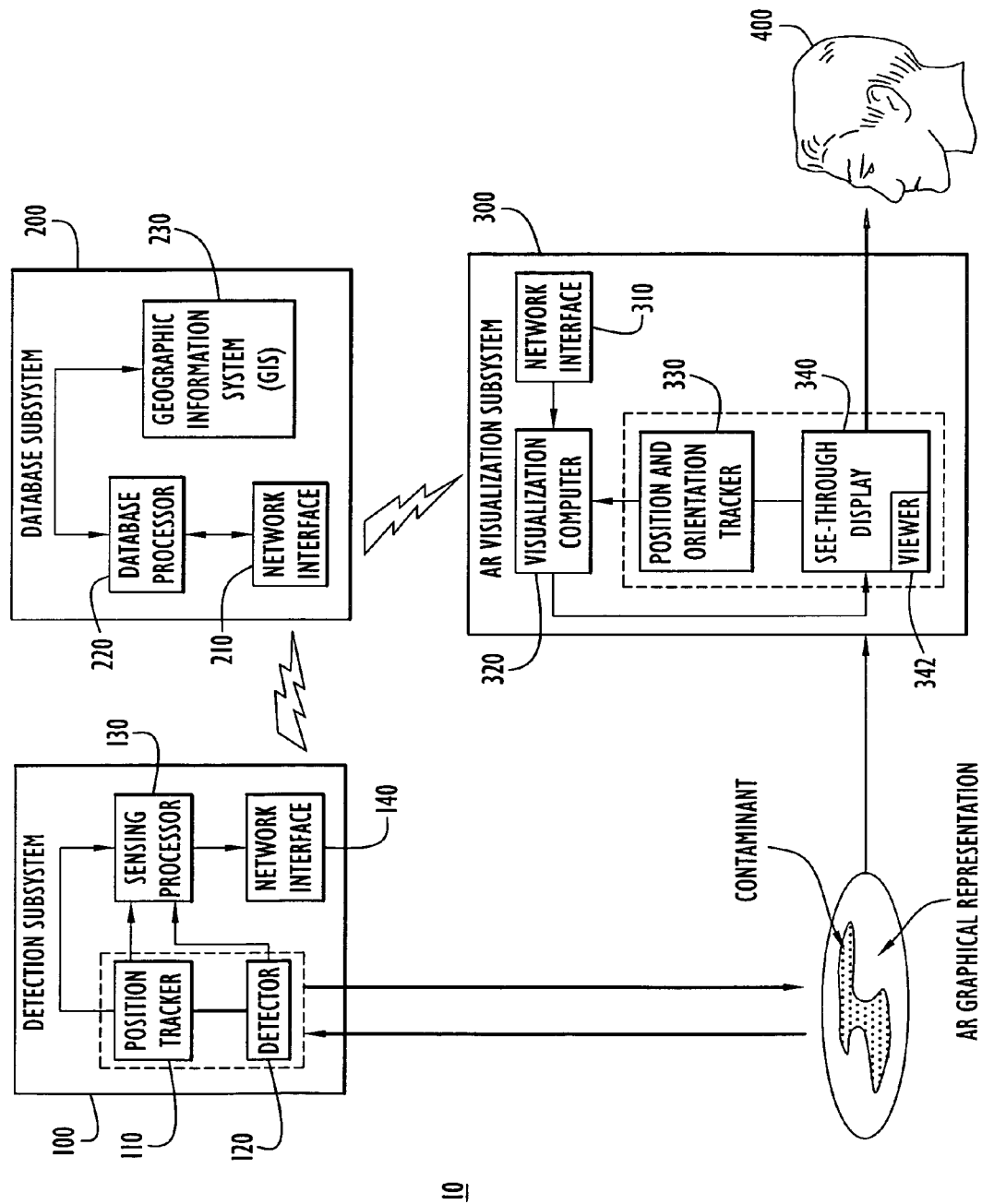
FIG. 1 is block diagram of a system according to an embodiment of the invention.

Referring first to FIG. 1, a system according to one embodiment of the invention is shown at reference 10 and comprises a detection subsystem or module 100, a database subsystem or module 200 and an augmented reality (AR) visualization subsystem or module 300. The detection subsystem 100 detects a substance and generates first data representing at least one characteristic of the substance. The detection subsystem 100 also determines positional information indicating where the substance is detected and generates second data representing the position of the detected substance. Furthermore, the detection subsystem 100 may generate positional information that indicates where the detection subsystem 100 has already scanned for substances (regardless of whether a substance has been detected) within a given area. The first and second data, which may be referred to as geo-referenced data, are supplied to the database subsystem 200. The database subsystem 200 logs the geo-referenced data into a database that stores the data for subsequent access by other systems. The AR visualization subsystem 300 generates display data for displaying the geo-referenced data overlaid on a real-world view of a scene using AR display techniques.

In the most general case, the subsystems 100, 200 and 300 may communicate through wireless or wired network links. However, two or all of these modules can be located on the same platform and communicate through shared memory. The AR visualization subsystem 300 accesses the data stored in the database subsystem 200 to create a three-dimensional (3D) model of the geo-referenced data which are graphically overlaid on the view of the environment using a tracked see-through display. The see-through display can be a video or optical see-through display as is commonly used in AR. An end user 400 looking at the display may also be looking at the collected data displayed at a remote platform, or may be the same person that is collecting data with use of the detection subsystem 100.

The detection subsystem 100 comprises a position tracker 110, a substance detector 120, a sensing processor 130 and a network or communication interface 140. The detector 120 examines a surface under consideration to detect a substance and determine at least one characteristic of a detected substance. The detector may be any type of chemical, biological or other sensor heretofore known or hereinafter developed. For example, and not by way of limitation, the detector 120 may incorporate one or more detection capabilities of the Laser Interrogation of Surface Agents (LISA) technology developed by ITT Corporation and which is disclosed in U.S. Pat. No. 6,788,407. The LISA system uses a laser that is directed onto the ground or any surface and based on a technique known as Raman Scattering (or Raman Effect), an optical property of the returned optical energy from the surface is analyzed to characterize or identify a chemical or biological substance on the surface using spectroscopy techniques.

The detector 120 may be integrated or mounted on any of a variety of different types of moving or movable platforms including a ground vehicle, a cart, a man-wearable device such as a backpack or waist pack, handheld devices alone or in combination with a man-wearable device, and unmanned devices such as robots, unmanned ground vehicles (UGVs) or unmanned air vehicles (UAVs). The techniques according embodiments of the present invention encompasses all of these platforms as possible implementations of the detection subsystem 100. In addition, the detector 120 may be integrated or mounted on a non-moving platform application such as a point sensor where the sample is brought into contact or proximity of the sensor. A point sensor may, for example, make microscopic sample characterization where the sample surface is scanned using a translation stage or a surface scanner. Yet another example of a non-moving detector platform configuration is any standoff sensor in a stationary position where the user presents the sample to a sensor collection aperture at varying sample-surface points for portal or checkpoint inspection, including package scanners using conveyor belts and manual check points where a user moves the object under the sensor.

The position tracker 110 is attached to the detector 120 and is used by the sensing processor 130 to determine the location where the detector 120 is scanning for substances to produce the position of the sample data. The position tracker 110 determines the position of a region in the scene where the detector is operating and its implementation is arbitrary. That is, any of a variety of positioning technologies may be employed to perform the function of the position tracker 110. For example, the position tracker 110 may use a global positioning system (GPS) device or an inertial navigation system (INS) device. The time component of the geo-referenced data may, depending on the type of position technology used, be supplied by the position tracker 110 or by a clock associated with the sensing processor 130.

The sensing processor 130 analyzes the data collected by the detector 120 to determine the composition (chemical or biological) of a substance. The sensing processor 130 may characterize the substance by determining its constituents and/or by identifying it by name. In addition, the sensing processor 130 may generate information indicating whether the substance is a hazard or threat to a human or other life. The geo-referenced data comprising the first data associated with a detected substance and the second data indicating the location where it was detected is sent by the network interface 140 to the database subsystem. The geo-referenced data may comprise data indicating: (a) the composition, name or name of constituents of the substance; (b) whether or not the substance is harmful, i.e., is a contaminant; (c) the time at which it was detected and (d) the position where the substance is detected. Since the position tracker 110 will also supply position data when a substance is not detected, the geo-referenced data often may include null set information for items (a) and (b), and the data for item (c) and (d) will be the time at which this data is collected and the position of the scanned area.

In the case where the detector 120 is integrated or mounted on a moving platform, the position tracker 110 may comprise one or more sensors used to determine the position and orientation of the detector 120 itself and a distance measurement sensor that determines the distance from the detector 120 to the surface being scanned or sampled. Using this information, a vector originating at the detector 120 and ending at the center of the surface being sampled can be constructed and used to determine the location of the sample. The sensors used to find the position and orientation of the detector 120 are, for example, gyroscopes, compass, accelerometers, geo-location-capable wireless networks (e.g. Mesh-Enabled Architecture) or a satellite navigation (e.g., GPS) device. Since standalone GPS might not be sufficiently accurate for certain applications, a differential or even real-time kinematic GPS with a base station may be employed. It is also possible to envision a system that would use GPS coordinates except for the height coordinate, which is derived from a very precise model of the elevation at the two-dimensional location produced from the GPS signals.

Alternatively, the position and orientation (attitude), of the moving detector can also be inferred by tracking its relative attitude with respect to another attitude-tracked structure. For example, in the case of a man-portable version of the detector 120, it might be desirable to track the position of the portable detector with respect to a nearby vehicle to provide high tracking accuracy without a large and heavy sensor to be mounted on the portable detector. In this case, the position data of the detector is referenced with respect to the vehicle, or geo-referenced if the attitude of the vehicle is tracked with respect to Earth. This is because only the position is needed for detecting a substance, whereas position and orientation, or attitude, are needed for the vehicle or the reference of the tracking system. Yet another position tracking technique is to use a backpack or other wearable unit that is carried by the user as the tracking reference, and then track the position of the wearable unit with respect to Earth.

There is also the case where an object to be scanned is moving but the detector is fixed in position. For example, the object may be moving along a conveyor belt and the detector is fixed in a position above the conveyor belt. In this case, a position sensor, such as an encoder on the conveyor belt, is provided to report the position of the conveyor belt and therefore of the object as it moves.

The detector-to-surface distance measurements may be performed by a variety of sensor devices. For example, and not by way of limitation, acoustic or optical sensor devices may be used. Alternatively, laser-based triangulation and time-of-flight distance sensors may be employed. Time-of-flight information can be obtained from a separate laser device or in the case of a Raman sensor can be obtained from the laser contained in the detector 120. The position tracker 110 can be simplified if the distance between the detector 120 and the surface is very small. For example, if the detector 120 is on a moving platform that can be brought close to the surface to be sampled, then the location of the detector 120 is about the same as the sample surface and in this case the position tracker 110 may comprise sensors that measure the position of the detector 120 without the need for any orientation or distance sensors.

The database subsystem 200 comprises a network or communication interface 210 that receives receiving the geo-referenced data from the detection subsystem 100, a database processor 220 that manages a database and a geographic information system (GIS) 230. The database processor 220 cooperates with the GIS 230 to store the geo-referenced data in a data structure that allows for subsequent efficient access and relates data to their spatial position. The GIS 230 may be as simple as a spatial tree-based data structure or as complex as a commercial GIS such as the ArcGIS system by ESRI. The database subsystem 200 provides access to the data in the database managed by the database processor 220 in response to requests received via the network interface 210.

The AR visualization subsystem 300 allows a user to see graphics superimposed on view of the physical environment or scene showing what kind of substances have been detected and where in the physical environment or scene the substances are detected. It also shows where the environment has been scanned. The AR visualization subsystem 300 comprises a network or communication interface 310, a visualization computer or processor 320, a position and orientation tracker 330 and a see-through display 340. The visualization computer 320 obtains the geo-referenced data through the network interface 310 by requesting it from the database subsystem 200.

The amount and spatial extent of the geo-referenced data requested depends on the resolution/size of the data needed and on the amount of local memory available in the visualization computer 320. For example, the processor 220 may take incoming geo-referenced point data and instead of naively storing the data in the GIS 230, the processor 220 would "create zones" and lines and store them using vector graphics rather than point data. Storing the contour of a shape as a series of vectors uses much less memory than storing all the point within the surface. The location of incoming geo-referenced point from the detection subsystem 100 would be compared to existing shapes in the database subsystem 200 and if the location is inside or close to the shape, then the shape could be extended to include this new point. This has implication on the amount of memory used to store the data in the database and more importantly on the speed at which the data can be extracted by the AR visualization subsystem 300 from the database subsystem 200.

The geo-referenced data is organized by the visualization computer 320 in a spatial data structure called a 3D model that is suitable to be displayed by a graphics rendering engine executed on the visualization computer 320.

The position and orientation tracker 330 determines the position and orientation of the field of view of the see-through display 340 with respect to the frame of reference that is used by the detector 120. For example, if the detector 120 uses an Earth-fixed referential then the position and orientation tracker 330 provides the attitude of the display 340 that is referenced to the same Earth-fixed referential. Similarly, it is possible that the detector's position may be tracked with respect to a nearby vehicle. In this case, the tracking of the see-through display 340 needs to be expressed in the same frame of reference. If a frame of reference used for tracking the position of the detector 120 is different from the frame of reference used for tracking the field of view of the see-through display 340, the visualization computer 320 converts the tracking data for the display 340 into the same frame of reference used to store the sampled substance data. For example, the position and orientation tracker 330 may comprise a combination of a GPS or INS sensor for position and a compass or gyroscope for orientation.

The visualization computer 320 renders the 3D model from the viewpoint of the display 340 by "projection", a process commonly used to render 3D graphics. This projection process creates a view of the 3D model as seen from the viewpoint of the display 340 and is performed several times per second, for example, so that as the viewpoint is changed the data produced by the visualization computer 320 is modified accordingly. The viewpoint thus represents position and orientation and the visualization computer 320 uses viewpoint to generate the visualization data by projecting it onto the display screen the image data that is sent to the see-through display 340 to be presented to the user 400.

The see-through display 340 shows a view of the environment as well as graphics generated by the visualization computer 320. The see-through display 340 comprises a viewer 342 that obtains a view of the environment. Examples of views presented on the see-through display 340 are shown and described hereinafter in conjunction with FIGS. 3-5. In AR visualization, the see-through display 340 overlays the image data generated by the visualization computer 320 on top of the view of the physical environment. There are two types of see-through displays heretofore known. One type is called a video see-through display, where the viewer 342 is a video camera that captures the view of the environment as seen by the user, the graphics produced by the visualization computer 320 are superimposed on top of the video image, and the resulting image is presented on a screen to the user. The other type is called an optical see-through display in which the viewer 342 is an optical beam-splitter that captures a view of environment or scene as seen by the user through an optical beam-splitter while the graphics produced by the visualization computer 320 are presented on a screen and are reflected by the same beam splitter toward the user's eye(s), in effect optically combining the graphics with the view of the environment. These are only examples of see-through displays and any other see-through display technique heretofore known or hereinafter developed may be used.

There are numerous exemplary platforms for the AR visualization subsystem 300. In one embodiment, the viewer 342 is a camera mounted on a vehicle (manned or unmanned) and a see-through display is connected to receive the video output of the camera and the geo-referenced data retrieved from the database subsystem 200 is overlaid on the video signal. In another embodiment, the see-through display 340 and the viewer (video camera) 342 are integrated in a head-mounted video see-through display. Similarly, the see-through display 340 may be a head-mounted optical see-through display device similar to eyeglasses because it shows the environment in front of the user and graphics.

The network/communication interfaces in the detection, database and AR visualization subsystems shown in FIG. 1 may be capable of performing wired or wireless communication either using any known or hereinafter developed networking protocols or standards. Alternatively, the interfaces may be capable of performing a customized wired or wireless communication protocol. To this end, it should be understood that the interfaces may comprise radio frequency (RF) transceivers, modems, and signal processors, necessary to perform the communication or networking functions.

Figure 2:
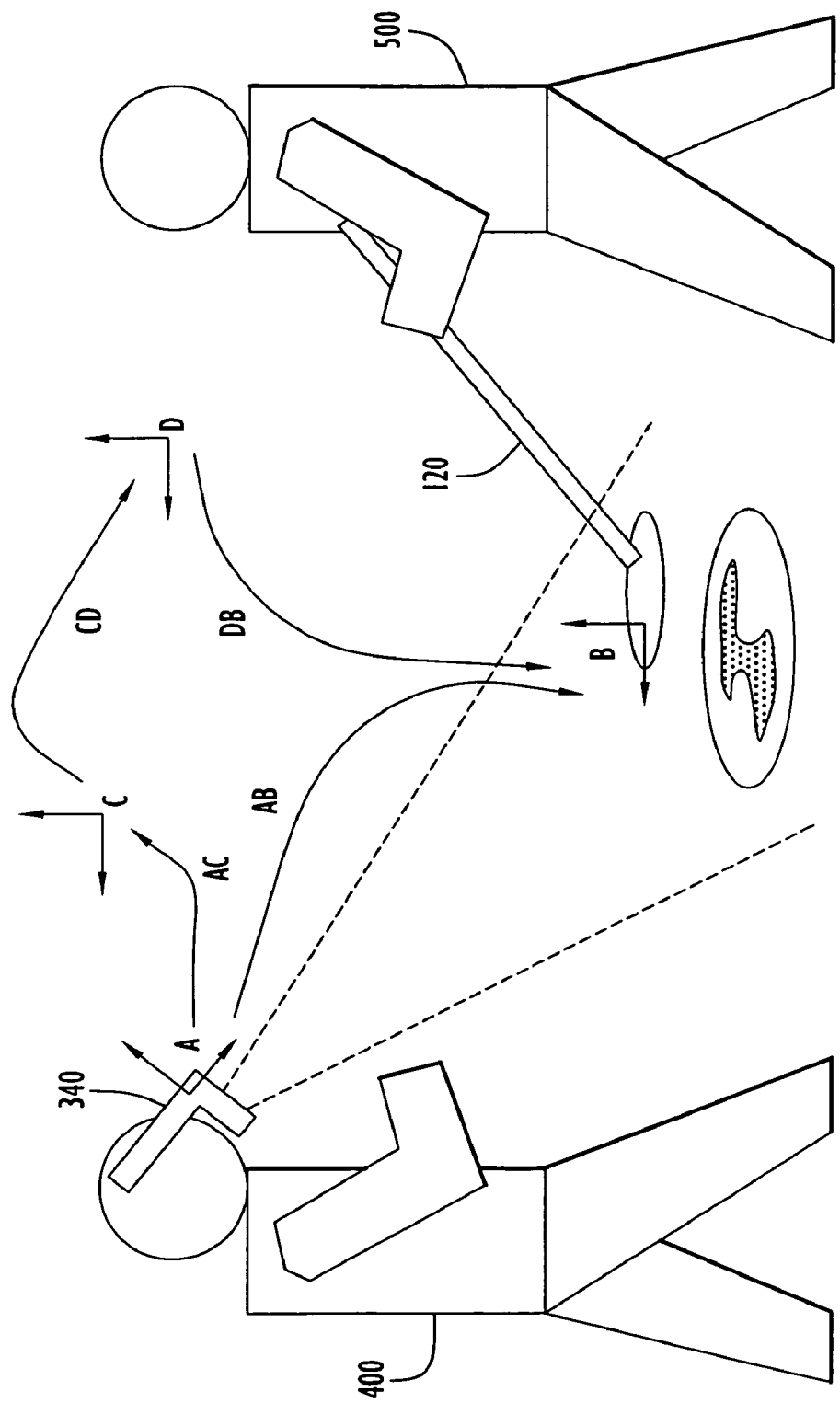
FIG. 2 is a diagram depicting operation of the system and the different coordinates systems involved in the creation of the database of detected samples and its representation through Augmented Reality (AR) according to an embodiment of the invention.

Reference is now made to FIG. 2, with continued reference to FIG. 1. The user 400 on the left is a user using a wearable version of the AR visualization subsystem 300 and the user 500 on the right is a user that is operating a man-portable detector 120. The user that operates the detector 120 may be the same user that uses the AR system 300. Alternatively, as indicated above, substance detection can be performed from a vehicle or a robot rather than by a user. Similarly, the AR visualization can be vehicle-mounted or fixed, instead of head-mounted on a user.

The see-through display 340 is shown on the head of the user 400. The display 340 has a frame of reference A that is tracked by the position and orientation (attitude) tracker 330 that gives the position and orientation (i.e. attitude) of the display reference frame A with respect to a first arbitrary frame of reference C. This is a transformation that changes reference frame A into reference frame C and is noted AC in FIG. 2. As one example, the position and orientation tracker 330 may use a combination of a GPS sensor for position and a compass for orientation and in this case the frame of reference C would be attached to the Earth.

The substance detector 120 is operated by user 500 and its position and orientation may vary. The position tracker 110 measures the position and orientation B of the detector with respect to a second arbitrary frame of reference D. As indicated above, and for this given configuration which is chosen to simplify the explanation, the position of a detected substance is considered to be the position B at the time of the collection, which is the same as the position of the detector 120 if the detector 120 is very close to the substance position. In this case, a GPS position sensor could be used for the position tracker 110. On the other hand, if the distance between the detector 120 and the surface on which a substance is detected is relatively large, the position tracker 110 may include an optical tracker that enables a determination of the position and orientation of the substance relative to the detector 120. The AC transformation may be the same as the BD transformation, and in this case, the reference frames C and D may be the same.

Figure 3:
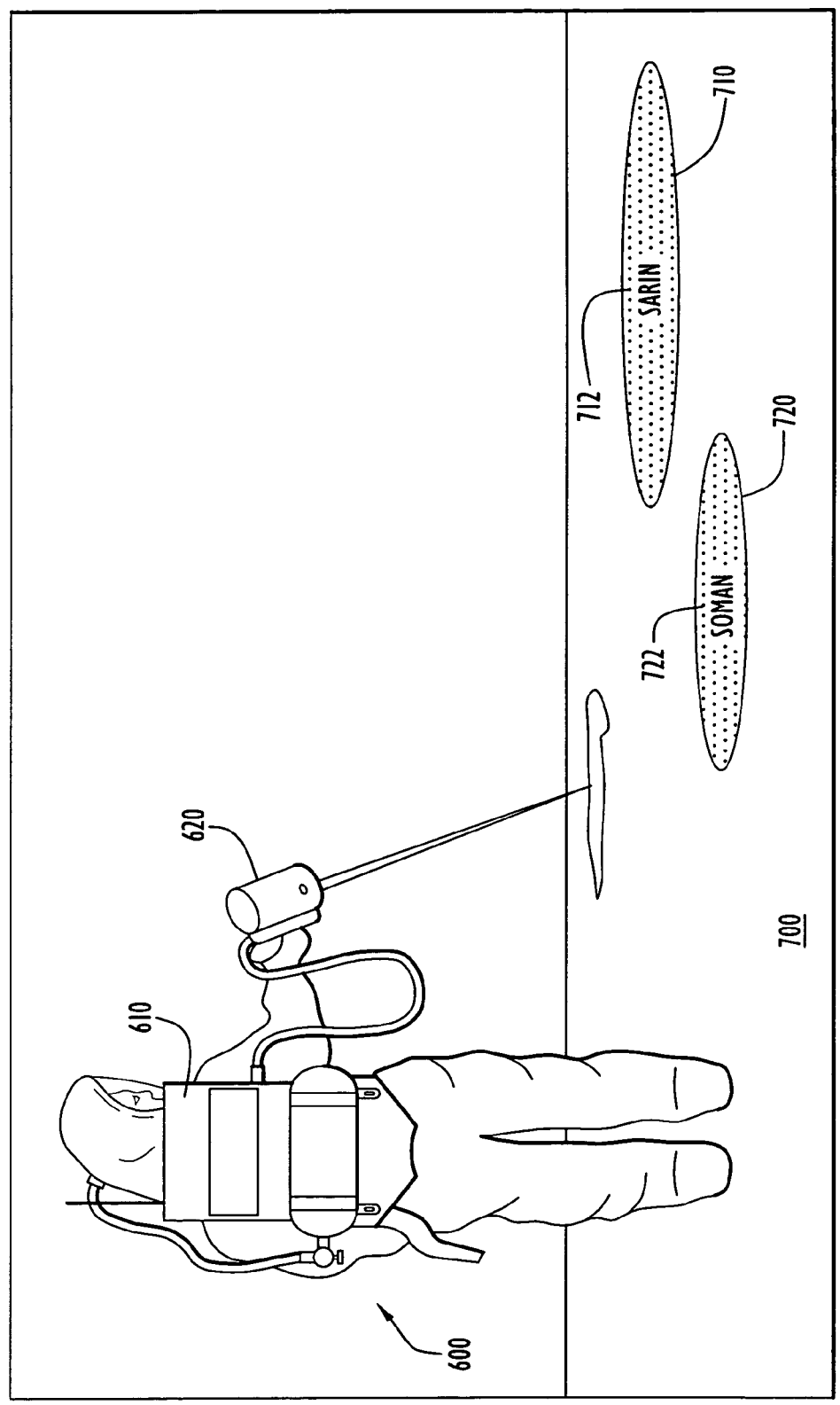
FIGS. 3-5 are diagrams showing exemplary display content according to various embodiments of the invention.
Figure 4:
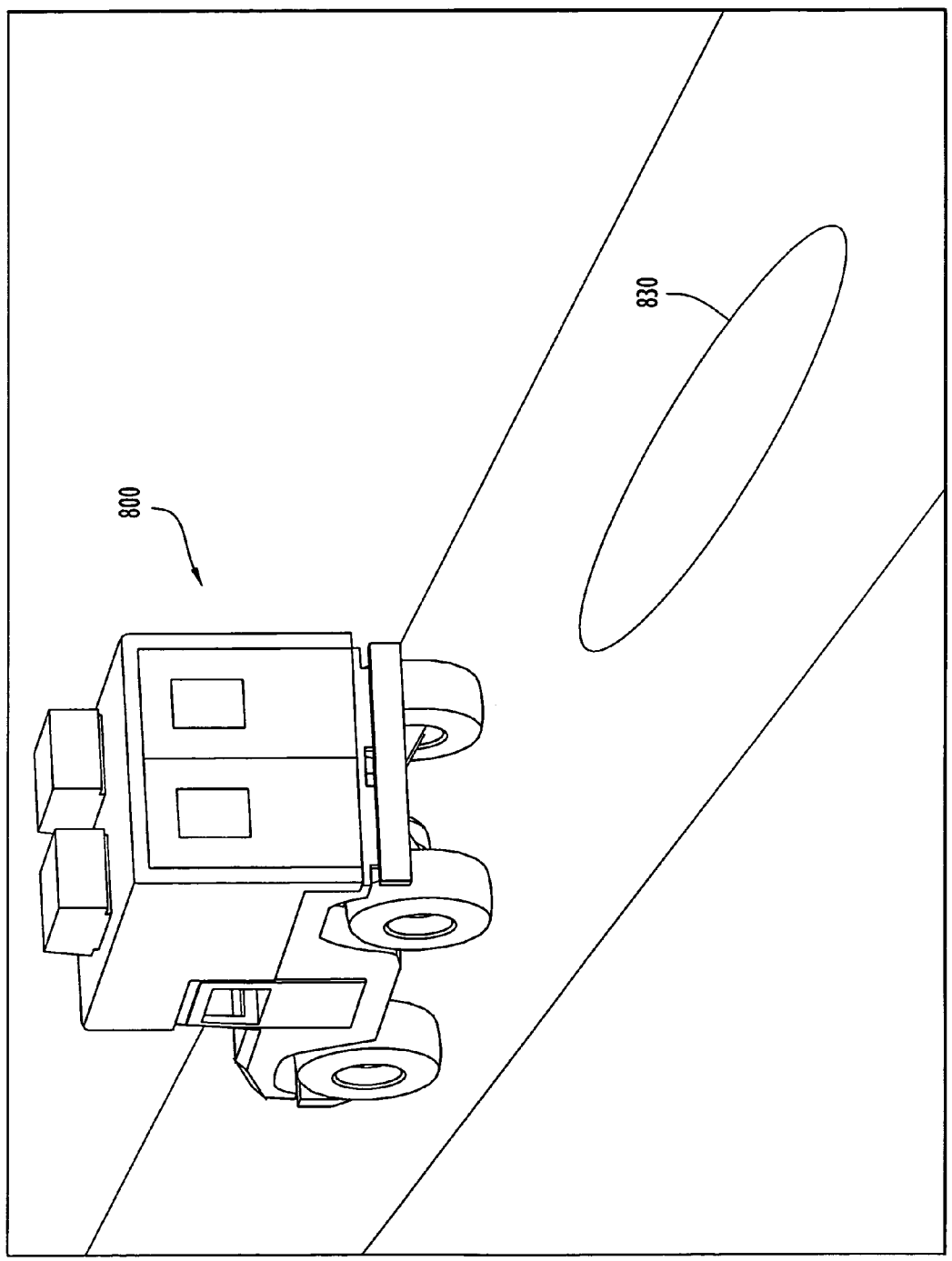
Figure 5:
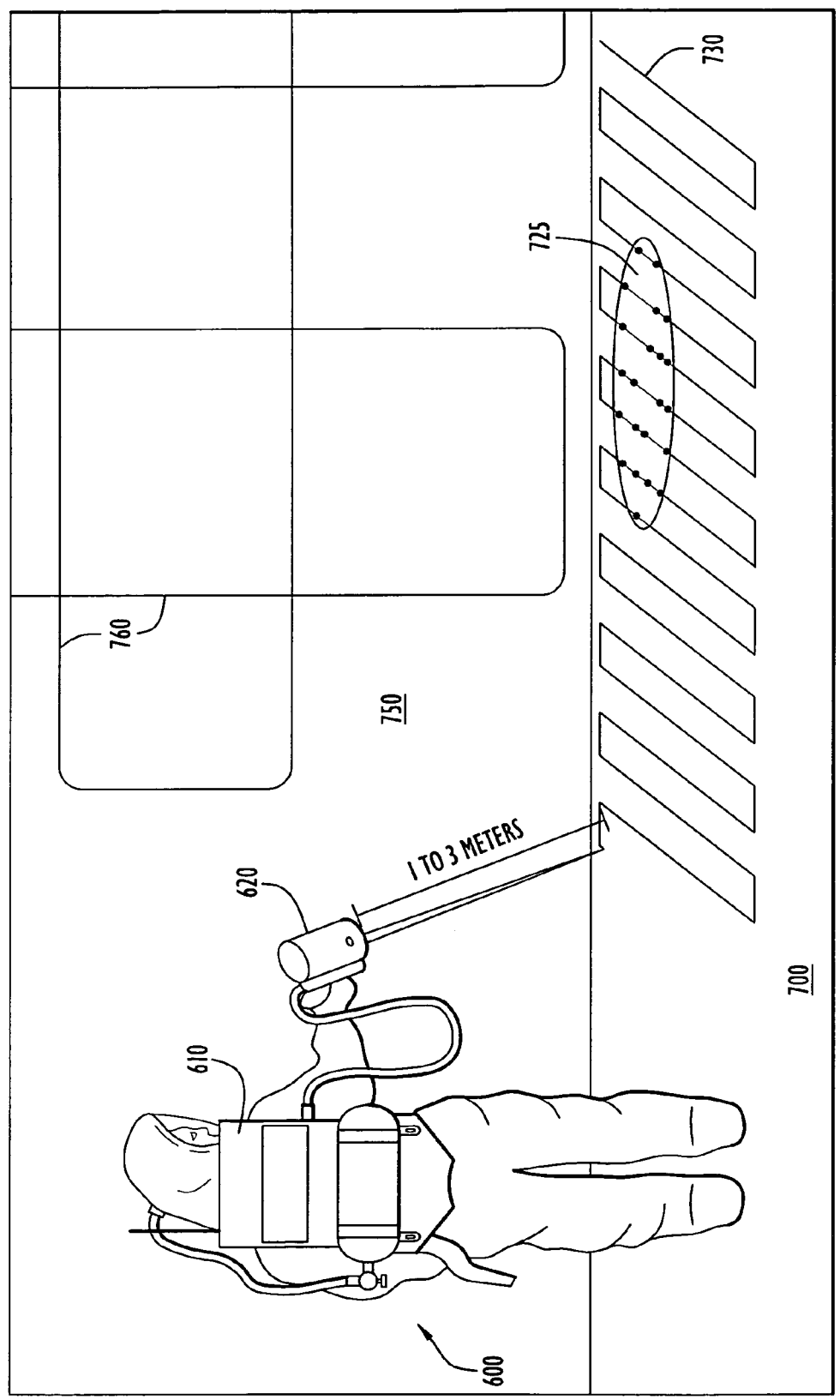

For the see-through display to show the correct graphics, the transformation AB needs to be known. By projecting the point B on the display through perspective projection, the graphics generated by the visualization computer will superimpose the real substance location in a real world reference frame view. The transformation AB is computed for each geo-referenced data set in order to display and generate the correct scenery by combining the transforms AC, CD and DB. In terms of matrix multiplications, this involves computing AB=AC×CD×DB. With reference to FIGS. 3-5, exemplary display content are shown so that the graphics being displayed have a semantic meaning that makes sense for the user using viewing the information. FIG. 3 illustrates exemplary display content comprising a scene viewed by the user on which labeled graphical element patches are overlaid that represent detected substances. The scene consists of a person 600 carrying a wearable detector apparatus comprised backpack portion 610 and a hand-held portion 620. The person 600 is directing a laser beam from the hand-held portion 620 to the ground surface shown at reference numeral 700. The graphical elements that represent the detected substances are shown at reference numerals 710 and 720 and include text (words and/or chemical symbol diagrams) labels 712 and 722, respectively for each substance, where label 712 identifies the graphical element patch 710 as Sarin and the label 722 identifies the graphical element patch 720 as Soman. The graphical element patches 710 and 720 can be made to have a color or other graphical attribute that stands out against the scene and that may distinguish harmful detected substances for non-harmful detected substances.

FIG. 4 illustrates another exemplary display content where the scene viewed by a user consists of a vehicle 800 driving (away from the viewing user) on a road. A graphic element representing a detected harmful substance is shown at reference numeral 830. The vehicle is equipped with a detector apparatus that, for example, is mounted to monitor the road surface beneath the chassis of the vehicle 800 as it travels along the road.

FIG. 5 illustrates exemplary display content where the scene viewed by the user is similar to the one shown in FIG. 3, except that graphical element lines are provided to indicate where in the scene the detector has already scanned for substances. For example, on the horizontal surface 700 (e.g., the ground), graphical element lines 730 are drawn to indicate where the detector has already scanned on the surface 700. A substance detection patch is shown at reference numeral 725. Similarly, on a vertical surface 750 (e.g., a wall), graphical element lines 760 are drawn to indicate where on the vertical surface 750 the detector has already scanned.

In the exemplary display content shown in FIGS. 3-5, different colors could be used for the graphical elements that represent different types of substances that have been detected or to differentiate areas that have been scanned from the areas that have not been scanned. The labels may provide more information about the type of substance detected and when (time, date) it was detected and by which sensor it was detected as well. More detailed information about the data collected at a given location could be displayed to the user of the AR visualization subsystem by moving a graphical element, e.g., a cursor or cross-hairs, to overlay that portion of the scene or by turning the center of the display toward a graphical element representing a substance detected in the scene.

As suggested above, the detection subsystem 100, the database subsystem 200, and the AR visualization subsystem 300 may all be running in a single application on the same hardware/computing platform or on separate platforms in several applications. The displayed information seen on the see-through display of the AR visualization subsystem 300 may also be made available over a data network (e.g., Internet) to enable a person at a remote site to view the scene and overlaid data on a standard computer monitor. In this case, since the person cannot see the environment through the display, it is necessary that the video of the scene is transmitted as well so that the graphics are overlaid on it.

One application of the system 10 involves a lead vehicle of a convoy equipped with a detection subsystem 100 that detects substances and references its scanning and detection activity with respect to Earth where the position tracker 110 comprises a GPS and/or INS navigation system capable of precisely producing the position of each detected substances. Vehicles in the convoy that follow the lead vehicle have a forward looking video camera that captures a view of the route in front and substances that have been detected by the leader vehicle are displayed directly on the scene viewed by the video camera on a screen placed in the driver's field of view in the following vehicles. Alternatively, the user in the vehicle could be using an optical see-through display, similar to eyeglasses, to view the overlay on the road. Another application of the system 10 involves a man-portable detection subsystem 100 carried or worn by a user that is tracked with reference to a nearby vehicle using a short-range high precision six degrees of freedom (6DOF) or other optical tracking system. The same user that carries the man-portable detection subsystem or another user who is nearby wears a video see-through display mounted in protective goggles which is tracked with the same vehicle-referenced tracking system. The user wearing the video see-through display can see real-time video of the scene augmented with graphical elements showing where data has been collected and where substances have been detected.

The system 10 provides for fast contact-free detection of substances, generation of a database containing the collected samples data along with their corresponding location information (geo-referencing), visualization of the geo-referenced data overlaid on the physical environment to any person or device that can access the database using an Augmented Reality (AR) display interface.

The system and techniques of the embodiments described herein provide for showing in an intuitive and practical way where and which types of surface-deposited substances have been detected in a contaminated scene. This collocated qualitative and spatial information can increase the responders' situational awareness, search strategies and safety by providing several functions. By overlaying color-coded or labeled graphical element patches on real-time display of the scene for regions in the scene where threat substances have been detected, these regions can be avoided by any person that can access and AR-visualize data stored in the database (e.g. surveyor, other responders, scene commander, etc.). The extent and level of contamination of a scene can be assessed by any person that can access and AR-visualize the data stored in the database. By visually contouring the real-time display of regions in the scene where threat substances are being detected, these regions can be better delineated by a substance detector operator. By overlaying color-coded tracks on the real-time display of regions in the scene that have already been surveyed, the status of a search can be made known to any person that can access and AR-visualize the data stored in the database.

As an alternative to an AR display, the techniques of the present invention may be used in connection with a map display, such as a satellite image map display. This would provide less real-world information than an AR display, but nevertheless may be suitable for certain application and cost-sensitive situations. For example, map display data, such as satellite imagery of an area may be panned automatically so that the current location is at the center of the display. The areas where substances have been detected are overlaid on the map data making it possible to see the areas to avoid or that the areas that have been scanned, without using a full blown AR system.

Another application of the system is to train operators to use a surface contaminant sensor. Instead of a pristine view of a real word scene, virtual data is generated that simulates a view of a contamination scene where a virtual substance is present. An operator is then deployed at the simulated contamination scene while operating the surface contaminant sensor. The surface contaminant sensor may take on any of the variations described herein, and may be man-portable or vehicle mounted, etc. With the use of the surface contaminant sensor, the scene is scanned and the virtual substance is detected and geo-referenced detection data representative the detected substance is generated. On a see-through display device, the virtual data simulating a view of the contamination scene is displayed and the displayed virtual view of the scene is augmented, using the techniques described herein, with the geo-referenced data representing detection of the virtual substance to show the detected substance in the view of the contamination scene. The distinction with previous described uses of the system is that the substance does not actually exist; its presence is merely simulated to train an operator on how to use the detection device and AR visualization interface. A virtually contaminated scene substantially reduces cost, increases operator's safety and decreases environmental impact. It also provides a good metric to evaluate training effectiveness (e.g. time to detect) since a given scene at a specified level of difficulty can be reused for different operators or at various stages of a training phase.

The system and methods described herein may be embodied in other specific forms without departing from the spirit or essential characteristics thereof. The foregoing embodiments are therefore to be considered in all respects illustrative and not meant to be limiting.

What is claimed is:

1. A method for visualizing a scene, comprising:
   scanning the scene with a substance detector to detect a substance in the scene;
   tracking scanning positions of the substance detector in the scene with respect to a first frame of reference;
   storing data representing three-dimensional scanning positions of the substance detector in the first frame of reference;
   displaying a view of the scene from a second frame of reference;
   tracking changes in a relationship between the first frame of reference and the second frame of reference due to changes in position and orientation of the substance detector and/or the view of the scene;
   retrieving the data representing the three-dimensional scanning positions of the substance detector in the first frame of reference;
   transforming the data from the first frame of reference to the second frame of reference, taking into account the changes in the relationship between the first frame of reference and the second frame of reference; and
   augmenting the displayed view of the scene with graphical element data that represents the three-dimensional scanning positions of the substance detector in the second frame of reference.

2. The method of claim 1, wherein said displaying comprises displaying the view of the scene in real-time as said scanning is performed.

3. The method of claim 2, wherein said scanning is performed at a first location in the scene and said displaying comprises displaying the view of the scene taken from said first location in the scene.

4. The method of claim 2, wherein said scanning is performed at a first location in the scene and said displaying comprises displaying the view of the scene taken from a second location.

5. The method of claim 4, and further comprising tracking changes in the view of the scene taken from the second location, and wherein augmenting is based on changes in the view of the scene.

6. The method of claim 5, wherein tracking further comprises tracking changes in the position and/or orientation of the substance detector, and wherein augmenting is based on changes in the view of the scene and changes in the position and/or orientation of the substance detector.

7. The method of claim 6, wherein tracking further comprises tracking changes in position and orientation of a detected substance relative to the substance detector, and wherein transforming comprises transforming a frame of reference for a position-referenced data set representing the detected substance and its position for display in the view of the scene.

8. The method of claim 1, wherein said scanning is performed by a substance detector on or part of one of: a first manned or unmanned vehicle, a first man-portable apparatus, and a stationary equipment, and said displaying is performed on a see-through display device on or part of one or more of: a second manned or unmanned vehicle and a man-wearable apparatus.

9. The method of claim 1, wherein augmenting comprises generating the graphical element data so as to represent progress of the substance detector scanning in said scene.

10. The method of claim 1, and further comprising determining a composition and/or name for substance that is detected by the substance detector, and wherein said augmenting generating data to display text for the composition and/or name of a detected substance.

11. The method of claim 10, wherein augmenting comprises generating an attribute for a graphical element for display in the displayed view of the scene, wherein the graphical element indicates whether or not that a detected substance is harmful.

12. The method of claim 10, wherein tracking comprises determining the scanning position of the substance detector with respect to Earth.

13. The method of claim 12, wherein tracking comprises generating geo-referenced data comprising first data representing the composition and/or name of a substance detected by the substance detector and second data representing the three-dimensional position of the detected substance.

14. The method of claim 13, wherein storing comprises storing said geo-referenced data in a database, and wherein retrieving comprises retrieving said geo-referenced data from said database and augmenting comprises generating the graphical element data based on said geo-referenced data.

15. The method of claim 1, wherein scanning comprises scanning a surface in said scene with the substance detector at a distance from said surface.

16. The method of claim 1, wherein said tracking further comprises determining a time when the substance detector detects a substance, said storing further comprises storing data representing the time when the substance detector detects a substance, and wherein augmenting comprises generating graphical data indicative of the time when the substance detector detected the detected substance for display in the displayed view.

17. A system for visualizing a scene that is monitored for substance contamination, comprising:
  a detection subsystem comprising a substance detector that scans the scene to detect a substance, and a position tracker that tracks scanning positions of the substance detector with respect to a first frame of reference; and
  a storage subsystem that stores data representing three-dimensional scanning positions of the substance detector in the first frame of reference;
  a visualization subsystem that displays a view of the scene in a second frame of reference, wherein the visualization subsystem retrieves data from the storage subsystem and transforms the data from the first frame of reference to the second frame of reference taking into account changes in a relationship between the first frame of reference and the second frame of reference due to changes in position and orientation of the substance detector and/or the view of the scene, and wherein the visualization subsystem augments the view of the scene with data that represents the three-dimensional scanning positions of the substance detector in the second frame of reference the displayed view of the scene with graphical element data.

18. The system of claim 17, wherein said visualization subsystem displays a view of the scene as said substance detector scans the scene.

19. The system of claim 17, wherein the detection subsystem and the visualization subsystem are collocated.

20. The system of claim 17, wherein said position tracker tracks changes in the position and/or orientation of the substance detector and the visualization subsystem comprises a position tracker that tracks changes in the view of the scene, and wherein the visualization system comprises a visualization processor that accounts for changes in the view of the scene and changes in the position and/or orientation of the substance detector when augmenting the displayed view with the graphical element data.

21. The system of claim 20, wherein said visualization processor further generates graphical element data that represents detection of a substance in the scene and a three-dimensional position of the substance detected in the scene.

22. The system of claim 21, wherein said visualization subsystem augments the view of the scene with graphical element data that represents scanning progress of the substance detector in the scene.

23. The system of claim 17, wherein said substance detector scans a surface in said scene at a distance from said surface.

24. The system of claim 17, wherein the substance detector is on or part of one of: a first manned or unmanned vehicle, a first man-portable apparatus, and a stationary equipment, and wherein said visualization subsystem comprises a see-through display device on or part of one or more of: a second manned or unmanned vehicle and a man-wearable apparatus.

25. The system of claim 17, wherein the detection subsystem determines a composition and/or name for said detected substance, and wherein said visualization subsystem comprises a visualization processor that generates graphical element data to the display text for the composition and/or name of said detected substance.

26. The system of claim 17, wherein the position tracker in the detection subsystem tracks the scanning positions of the substance detector with respect to Earth.

27. The system of claim 26, wherein said detection subsystem comprises a processor that generates geo-referenced data comprising first data representing the composition and/or name of a detected substance and second data representing a three-dimensional geo-referenced position of the detected substance and a time when the substance detector detects a detected substance.

28. The system of claim 27, wherein the storage subsystem comprises a database that stores the geo-referenced data, and wherein said visualization subsystem retrieves the geo-referenced data from which it generates the graphical element data.

29. The system of claim 28, wherein the visualization subsystem and said database subsystem each further comprise a communication interface that enables communication between each other.

30. The system of claim 29, wherein the detection subsystem further comprises a communication interface that enables communication with said database subsystem.

31. The system of claim 30, wherein the detection subsystem, database subsystem and visualization subsystem are at different locations, and wherein the communication interfaces enable wireless communication between the subsystems.

32. A method for training operators to the use of a surface contaminant sensor, comprising:
  a. generating virtual data simulating a view of a contamination scene where a virtual substance is present;
  b. deploying the operator at the simulated contamination scene while operating the surface contaminant sensor;
  c. detecting the virtual substance in the scene with the surface contaminant sensor and generating geo-referenced detection data representative thereof; and
  d. displaying the virtual data simulating a view of the contamination scene;
  e. augmenting the displayed view of the contamination scene with said geo-referenced data representing detection of the virtual substance to show the detected substance in the view of the contamination scene.

33. A method for displaying data associated with a scene that is monitored for substance contamination, comprising:
  scanning the scene with a substance detector to detect a substance in the scene;
  tracking scanning positions of the substance detector in the scene with respect to a first frame of reference;
  storing data representing three-dimensional geo-referenced scanning positions of the substance detector in the first frame of reference;
  displaying video images for a three-dimensional view of the scene from a second frame of reference;
  tracking changes in a relationship between the first frame of reference and the second frame of reference due to changes in position and orientation of the substance detector and/or the view of the scene;

retrieving the data representing the three-dimensional geo-referenced scanning positions of the substance detector in the first frame of reference;

transforming the data from the first frame of reference to the second frame of reference, taking into account the changes in the relationship between the first frame of reference and the second frame of reference; and augmenting the displayed video images of the scene with graphical element data that represents the three-dimensional scanning positions of the substance detector in the second frame of reference.

34. The method of claim 33, wherein displaying comprises displaying map image data of the scene, and augmenting comprises augmenting the map image data with the graphical element data.

35. The method of claim 33, wherein displaying comprises display video images for a real-time view of the scene, and augmenting comprises augmented the real-time view of the scene with the graphical element data.

36. A method for visualizing a scene that has been scanned by a sensor for hazardous substances, comprising:

retrieving from a database data representing geo-referenced three-dimensional scanning positions of the sensor in a first frame of reference as the sensor is scanned through areas of the scene, wherein the data includes indications, if any, of substances detected by the sensor and geo-referenced three-dimensional positions of such detections in the scene;

displaying a real-time view of the scene from a second frame of reference;

tracking changes in a relationship between the first frame of reference and the second frame of reference due to changes in position and orientation of the view of the scene;

transforming the data from the first frame of reference to the second frame of reference, taking into account the changes in the relationship between the first frame of reference and the second frame of reference; and augmenting the view of the scene with graphical element data that represents the three-dimensional scanning positions of the substance detector in the second frame of reference.

37. A system, comprising:

a database storage subsystem that stores data representing geo-referenced three-dimensional scanning positions of a sensor in a first frame of reference as the sensor is scanned through areas of a scene, wherein the data includes indications, if any, of substances detected by the sensor and geo-referenced three-dimensional positions of such detections in the scene; and a display subsystem that displays a real-time view of the scene from a second frame of reference, wherein the display subsystem comprises a processor that tracks changes in a relation between the first frame of reference and the second frame of reference due to changes in position and orientation of the view of the scene, transforms the data from the first frame of reference to the second frame of reference taking into account changes in the relationship between the first frame of reference and the second frame of reference, and augments the view of the scene with graphical element data that represents the three-dimensional scanning positions of the substance detector in the second frame of reference.

* * * * *